(12) United States Patent
Miller et al.

(10) Patent No.: US 7,939,327 B2
(45) Date of Patent: *May 10, 2011

(54) SIMULTANEOUS MODULATION OF MULTIPLE GENES

(75) Inventors: Jeffrey Miller, Richmond, CA (US); Guofu Li, Johnston, IA (US); Carl Pabo, Mill Valley, CA (US); Trevor Collingwood, Novato, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 12/072,871

(22) Filed: Feb. 28, 2008

(65) Prior Publication Data

US 2008/0233641 A1 Sep. 25, 2008

Related U.S. Application Data

(62) Division of application No. 10/651,761, filed on Aug. 29, 2003, now Pat. No. 7,361,635.

(60) Provisional application No. 60/406,864, filed on Aug. 29, 2002.

(51) Int. Cl.
*C12N 15/82* (2006.01)
*C12N 5/14* (2006.01)

(52) U.S. Cl. .................................. 435/468; 435/419

(58) Field of Classification Search ..................... None
See application file for complete search history.

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid et al. |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Ma |
| 5,830,721 A | 11/1998 | Stemmer et al. |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,160,091 A | 12/2000 | Peukert et al. |
| 6,207,446 B1 | 3/2001 | Szostak et al. |
| 6,242,568 B1 | 6/2001 | Barbas, III et al. |
| 6,313,280 B1 | 11/2001 | Verschueren et al. |
| 6,607,882 B1 * | 8/2003 | Cox et al. ........................ 435/6 |
| 7,151,201 B2 * | 12/2006 | Barbas et al. ................. 800/278 |
| 2002/0035246 A1 | 3/2002 | Verschueren et al. |
| 2003/0044809 A1 | 3/2003 | Huylebroeck et al. |

FOREIGN PATENT DOCUMENTS

| | | |
|---|---|---|
| EP | 0 875 567 A2 | 4/1998 |
| WO | WO 92/02536 | 2/1992 |
| WO | WO 95/11922 | 5/1995 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 98/55512 | 12/1998 |
| WO | WO 99/36553 | 7/1999 |
| WO | WO 99/41371 | 8/1999 |

(Continued)

OTHER PUBLICATIONS

Wilson (PNAS, 2008. vol. 105, No. 15, pp. 5653-5654).*
Wu et al. (Cellular and Molecular Life Science, 2007. vol. 64, pp. 2933-2944).*
Agarwal et al., "Stimulation of Transcript Elongation Requires Both the Zinc Finger and RNA Polymerase II Binding Domains of Human TFIIS," Biochemistry 30(31): 7842-7851 (1991).
Antao et al., "A Thermodynamic Study of Unusually Stable RNA and DNA Hairpins," Nuc. Acids. Res. 19(21): 5901-5905 (1991).
Barbas, C.F. "Recent Advances in Phage Display," Curr. Opin. Biotech. 4: 526-530 (1993).

(Continued)

*Primary Examiner* — Celine X Qian
(74) *Attorney, Agent, or Firm* — Dahna S. Pasternak; Robins & Pasternak LLP

(57) ABSTRACT

Disclosed herein are compositions and methods that regulate expression of two or more endogenous genes.

17 Claims, 7 Drawing Sheets

FOREIGN PATENT DOCUMENTS

| | | |
|---|---|---|
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 00/41566 | 7/2000 |
| WO | WO 00/42219 A1 | 7/2000 |
| WO | WO 00/47775 | 8/2000 |
| WO | WO 01/00864 A2 | 1/2001 |
| WO | WO 01/19981 A2 | 3/2001 |
| WO | WO 01/83819 A3 | 3/2001 |
| WO | WO 01/79472 * | 10/2001 |
| WO | WO 02/063022 A2 | 8/2002 |
| WO | WO 02/066640 A2 | 8/2002 |
| WO | WO 03/016496 A2 | 2/2003 |

OTHER PUBLICATIONS

Barbas et al., "Assembly of Combination Antibody Libraries on Phage Surfaces: The Gene III Site," PNAS 88: 7978-7982 (1991).

Barbas et al., "Semisynthetic Combinatorial Antibody Libraries: A Chemical Solution to the Diversity Problem," PNAS 89: 4457-4461 (1992).

Beerli et al., "Toward Controlling Gene Expression at Will: Specific Regulation of the ERBB-2/HER-2 Promoter by Using Polydactyl Zinc Finger Proteins Constructed From Modular Building Blocks," PNAS 95: 14628-14633 (1998).

Beerli et al., "Positive and Negative Regulation of Endogenous Genes by Designed Transcription Factors," PNAS 97: 1495-1500 (2000).

Bellefroid et al., "Clustered Organization of Homologous Krab Zinc-Finger Genes With Enhanced Expressoin in Human T Lymphoid Cells," EMBO J. 12(4): 1363-1374 (1993).

Berg, J.M., "DNA Binding Specificity of Steroid Receptors," Cell 57: 1065-1068 (1989).

Berg, J.M., "SP1 and the Subfamily of Zinc-Finger Proteins With Guanine-Rich Binding Sites," PNAS 89: 11109-11110 (1992).

Berg et al., "The Galvanization of Biology: A Growing Appreciation for the Roles of Zinc," Science 271: 1081-1085 (1996).

Berg, J.M., "Letting Your Fingers Do the Walking," Nature Biotechnology 15: 323 (1997).

Bergqvist et al., "Loss of DNA-Binding and New Transcriptiional Trans-Activiation Function in Polyomavirus Large T—Antigen With Mutation of Zinc Finger Motif," Nature Biotechnology 18(9): 2715-2720 (1990).

Blaese et al., "Vectors in Cancer Therapy: How Will They Deliver?" Cancer Gene Therapy 2(4): 291-297 (1995).

Bonde et al., "Ontogeny of the V-ERBA Oncoprotein From the Thyroid Hormone Receptor: An Alteration in the DNA Binding Domain Plays a Role Crucial for Verba Function," J. Virology 65(4): 2037-2046 (1991).

Caponigro et al., "Transdomination Genetic Analysis of a Growth Control Pathway," PNAS 95: 7508-7513 (1998).

Celenza et al., "A Yeast Gene That is Essential for Release From Glucose Repression Encodes a Protein Kinase," Science 233: 1175-1180 (1986).

Cheng et al., "Identification of Potential Target Genes for ADRLP Through Characterization of Essential Nucleotides in UAS1," Mol. Cellular Biol. 14(6): 3842-3852 (1994).

Cheng et al., "A Single Amino Acid Subsitution in Zinc Finger 2 of ADRLP Changes Its Binding Specificity at Two Positions in UAS1," J. Mol. Boil. 251: 1-8 (1995).

Choo et al., "Designing DNA-Binding Proteins on the Surface of Filamentous PHaGE," Curr. Opin. Biotechnology 6: 431-436 (1995).

Choo et al., "Physicial Basis of Protein-DNA Recognition Code," Curr. Opin. Struct. Biol. 7(1): 117-125 (1997).

Choo et al., "Promoter-Specific Activiation of Gene Expression Directed by Bacteriophage-Selected Zinc Fingers," J. Mol. Biol. 273: 525-532 (1997).

Choo et al., "In Vivo Repression by a Site-Specific DNA-Binding Protein Deisned Against an Onogenic Sequence," Nature 372: 642-645 (1994).

Choo et al., "All Wrapped Up," Nature Struct. Biol. 5(4): 253-255 (1998).

Choo, Y., "Recognition of DNA Methylation by Zinc Fingers," Nature Struct. Biol. 5(4): 264-265 (1998).

Choo, Y., "End Effects in DNA Recognition Code," Nuc. Acids. Res. 26(2): 554-557 (1998).

Choo et al., "A Role in DNA-Binding for the Linker Sequences of the First Three Zinc Fingers of TFIIIA" Nuc. Acids Res. 21(15): 3341-3346 (1993).

Choo et al., "Toward a Code for the Interactions of Zinc Fingers With DNA: Selection of Randomized Fingers Displayed on Phage," PNAS 91: 11163-11167 (1994).

Choo et al., "Selection of DNA Binding Sites for Zinc Fingers Using Randomized DNAs Reveals Coded Interactions," PNAS 91: 11168-11172 (1994).

Clarke et al., "Zinc Fingers in *Caenorhabditis elegans*: Finding Familiies and Probing Patheways," Science 282: 2018-2022 (1998).

Comijn et al., "The Two-Handed E Box Binding Zinc Finger Protein SIP1 Downregulates E-cadherin and Induces Invasion," Molecular Cell 7: 1267-1278 (2001).

Corbi et al., "Synthesis of a New Zinc Finger Peptide: Comparison of Its "Code" Deduced and "Casting" Derived Binding Sites," FEBS Letters 417: 71-74 (1997).

Crozatier et al., "Single Amino Acid Exchanges in Separate Domains of the *Drosophilia* Serendipity Zinc Finger Protein Cause Embroyonic and Sex Biased Lethality," Genetics 131: 905-916 (1992).

Debs et al., "Regulation of Gene Expression In Vivo by Liposome-Mediated Delivery of a Purified Transcription Factor," J. Biological Chemistry 265(18): 10189-10192 (1990).

DesJardins et al., "Repeated CT Elements Bound by Zinc Finger Proteins Control the Absolute and Relative Activities of the Two Principal Human C-MYC Promoters," Mol. Cell. Biol. 13(9): 5710-5724 (1993).

Desjarlais et al., "Redesigning the DNA-Binding Specificity of a Zinc Finger Protein: A Data Base-Guided Approach," Proteins: Structure, Function, and Genetics 12(2): 101-104 (1992).

Desjarlais et al., "Redesigning the DNA-Binding Specificity of a Zinc Finger Protein: A Data Base-Guided Approach," Proteins: Structure, Function, and Genetics 13(2): 272 (1992).

Desjarlais et al., "Toward Rules Relating Zinc Finger Protein Sequences and DNA Binding Site Preferences," Proc Natl Acad Sci US A 89:7345-7349 (1992).

Desjarlais et al., "Use of a Zinc-Finger Consensus Sequences Framework and Specificity Rules to Design Specific DNA Binding, Proteins" PNAS 90: 2256-2260 (1993).

Desjarlais et al., "Length-Encoded Multiplex Binding Site Determination: Application to Zinc Finger Proteins," PNAS 91: 11099-11103 (1994).

Dibello et al., "The *Drosophila* Broad-Complex Encodes a Family of Related Proteins Containing Zinc Fingers," Genetics 129: 385-397 (1991).

Donze et al., "Activation of Delta-Globin Gene Expression by Erythroid Krupple-Like Factor: A Potential Approach for Gene Therapy of Sickle Cell Disease," Blood 88: 4051-4057 (1996).

Dreier, et al., "Development of Zinc Finger Domains for Recognition Od the 5'-Ann-3' Family of DNA Sequences and Their Use in the Construction Artificial Transcription Factors," J. of Biol Chem 276:29466-29478 (2001).

Effertz et al., "Strategies for the Regulation of Multiple Genes With Zinc Finger Transcription Factors," Molecular Therapy 5:S141, #432 (2002).

Elrod-Erickson et al., "ZIF2268 Protein-DNA Complex Refined At 1.6: A Model System for Understanding Zinc Finger-DNA Interactions," Structure 4(10): 1171-1180 (1996).

Elrod-Erickson et al., "High-Resolution Structures of Variant ZIF268-DNA Complexes: Implications for Understanding Zinc Finger-DNA Recognition," Structure 6(4): 451-464 (1998).

Fairall et al., "The Crystal Structure of a Two Zinc-Finger Peptide Reveals an Extension to the Rules for Zinc-Finger/ DNA Recognition," Nature 366: 483-487 (1993).

Frankel et al., "Fingering Too Many Proteins," Cell 53: 675 (1988).

Friesen et al., "Phage Display of RNA Binding Zinc Fingers From Transcription Factor IIA," J. Biological Chem. 272(17): 10994-10997 (1997).

Friesen et al., "Specific RNA Binding Proteins Constructed From Zinc Fingers," Nature Structural Biology 5(7): 543-546 (1998).

Fujimoto et al., "*Arabidopsis* Ethylene-Responsive Element Binding Factors Act As Transcriptional Activators or Repressors of GCC Box-Mediated Gene Expression," Plant Cell 12:393-404 (2000).

Ghosh, "A Relational Database of Teranscription Factors," Nucleic Acids Res. 18: 1749-1756 (1990).

Gillemans et al., "Altered DNA Binding Specificity Mutants of EKLF and SPL Show That EKLF is an Activator of the B-Globin Locus Control Region in Vivo," Genes and Development 12: 2863-2873 (1998).

Goff et al., "Indentification of Functional Domains in the Maize Transcirptional Activator Cl: Comparison of Wild-Type and Dominant Inhibitor Proteins," Genes Dev 5:298-309 (1991).

Gogos et al., "Recognition of Diverse Sequences by Class 1 Zinc Fingers: Asymmetries and Indirect Effects on Specificty in the Interaction Between CF2II and a+T-Rich Sequences Elements," PNAS 93(5): 2159-2164 (1996).

Gossen et al., "Tight Control of Gene Expression in Mammalian Cells by Tetracycline-Responsive Promoter," PNAS 89:5547-5551 (1992).

Greisman et al., "A General Strategy for Selecting High-Affinity Zinc Finger Proteins for Diverse DNA Target Sites," Science 275: 657-661 (1997).

Hall et al., "Functional Interaction Between the Two Zinc Finger Domains of the V-ERBA Oncoprotein," Cell Growth & Differentiation 3: 207-216 (1992).

Hamilton et al., "High Affinity Binding Sites for the Wilms' Tumor Suppressor Protein WTI," Nuc. Acids. Res. 23(2): 277-284 (1995).

Hamilton et al., "Comparison of the DNA Binding Characteristics of the Related Zinc Finger Proteins WT1 and EGR1" Biochemistry 37: 2051-2058 (1998).

Hanas et al., "International Deletion Mutants of Zenopus Transcription Factor 111A," Nuc. Acids. Res. 17(23): 9861-9870 (1989).

Hayes et al., "Locations of Contacts Between Individual Zinc Fingers Xenopus Laevis Transcription Factor 111A and the Internal Control Region of a 5S RNA Gene," Biochemistry 31: 11600-11165 (1992).

Heinzel et al., "A Complex Containing N-CoR, Msin3 and Histone Deacetylese Medates Transcriptional Repression," Nature 387: 43-48 (1997).

Hirst et al., "Discrimination of DNA Response Elements for Thyroid Hormone and Estrogen Is Dependent on Dimerization of Receptor DNA Binding Domains, " PNAS 89: 5527-5531 (1992).

Hoffman et al., "Structures of DNA-Binding Mutant Zinc Finger Domains: Implications for DNA Binding," Protein Science 2: 951-965 (1993).

Imhof et al., "Transcriptional Regulation of the AP-2 Alpha Promoter by BTEB-1 and AP-2REP, a Novel WT-1/EGR-Related Zinc Finger Repressor," Molecular and Cellular Biology 19(1): 194-204 (1999).

Isalan et al., "Synergy Between Adjacent Zinc Fingers in Sequence-Specific DNA Recognition," PNAS 94(11): 5617-5621 (1997).

Isalan et al., "Comprehensive DNA Recogniition Through Concerted Interactions From Adjacent Zinc Fingers," Biochemistry 37:12026-12033 (1998).

Isalan et al., "Engineered Zinc Finger Proteins That Respond to DNA Modification by HAEIIIand HHAI Methyltransferase Enzymes," J Mol Biol 295:471-477 (2000).

Isalan et al., "A Rapid, Generally Applicable Method to Engineer Zinc Fingers Illustrated by Targetting the HIV-1 Promoter," Nat Biotechnol 19:656-660 (2001).

Isalan et al., "Rapid, High-Throughput Engineering of Sequence-Specific Zinc Finger DNA-Binding Proteins," Methods Enzymol 340:593-609 (2001).

Iuchi, "Three Classes of C2H2 Zinc Finger Proteins," Cellular and Molecular Life Sciences 58:625-635 (2001).

Jacobs, G. H., "Determination of the Base Recognition Positions of Zinc Fingers From Sequence Analysis," EMBO J. 11(12): 4507-4517 (1992).

Jamieson et al., "A Zinc Finger Directory for High-Affinity DNA Recognition," PNAS 93: 12834-12839 (1996).

Jamieson et al., "In Vitro Selection of Zinc Fingers With Altered DNA-Binding Specificity," Biochemistry 33:5689-5695 (1994).

Jones et al., "Replacing the Complementarity-Determining Regions in a Human Antibody With Those From Mouse," Nature 321: 522-525 (1986).

Joung et al., "A Bacterial Two-Hybrid Selection System for Studying Protein-DNA and Protein-Protein Interactions," Proc. Natl. Acad. Sci. USA 97:7382-7387 (2000).

Julian et al., "Replacement of HIS23 by CYS in a Zinc Finger of HIV-1NCP7 Led to a Change in 1H NMR-Derived 3D Structure and to a Loss of Biological Activity," FEBS Letters 331(1,2): 43-48 (1993).

Kamiuchi et al., "New Multi Zinc Finger Protein: Biosynthetic Design and Characteristics of DNA Recognition," Nucleic Acids Symposium Series 37: 153-154 (1997).

Kang et al., "Characterization of Salicylic Acid-Responsive, Arabidopsis Dof Domain Proteins: Overexpression of OBP3 Leased to Growth Defects," Plant J 21:329-339 (2000).

Kang et al., "Zinc Finger Proteins as Designer Transcription Factors," J. Biol. Chem. 275(12):8742-8748 (2000).

Keller et al., "Metabolic Compartmentation of Plastid Prenyllipid Biosynthesis—Evidence for the Involvement of a Multifunctional Geranylgeranyl Reductase," European Journal of Biochemistry 251:413-417 (1998).

Kim et al., "Serine at Position 2 in the DNA Recognition Helix of a CYS2-HIS2 Zinc Finger Peptide is Not, in General, Responsible for Base Recognition," J. Mol. Biol. 252: 1-5 (1995).

Kim et al., "Site-Specific Cleavage of DNA-RNA Hybrids by Zinc Finger/Folk/Cleavage Domain Fusions," Gene 203: 43-49 (1997).

Kim et al., "A 2.2 A° Resolution Crystal Structure of a Designed Zinc Finger Protein Bound to DNA," Nat. Struct. Biol. 3(11): 940-945 (1996).

Kim et al., "Design of Tata Box-Binding Protein/Zinc Finger Fusions for Targeted Regulation of Gene Expression," PNAS 94: 3616-3620 (1997).

Kim et al., "Hybrid Restriction Enzymes: Zinc Finger Fusions FOK 1 Cleavage Domain," PNAS 93: 1156-1160 (1996).

Kim et al., "Transcriptional Repression by Zinc Finger Peptides. Exploring the Potential for Application in Gene Therapy" J. Biol. Chem. 272: 29795-29800 (1997).

Kim et al., "Getting a Handhold on DNA: Design of Poly-Zinc Finger Proteins With Femtomolar Dissociation Constants," Proc Natl Acad Sci U S A 95:2812-7 (1998).

Kinzler et al., "The GLI Gene Is Member of the Kruppel Family Zinc Finger Proteins," Nature 332: 371-374 (1988).

Klug, A. "Gene Regulatory Proteins and Their Interaction With DNA," Ann. NY Acad. Sci. 758: 143-160 (1995).

Klug et al., "Protein Motifs 5: Zinc Fingers," FASEB J. 9: 597-604 (1995).

Klug, "Zinc Finger Peptides for the Regulation of Gene Expression," J. Mol. Biol. 293: 215-218 (1999).

Kothekar, "Computer Simulation of Zinc Finger Motif From Cellular Nucleic Acid Binding Proteins and Their Interaction With Consensus DNA Sequences," FEBS Letters 274(1,2): 217-222 (1990).

Kriwacki et al., "Sequence-Specific Recognition of DNA by Zinc Finger Peptides Derived From the Transcription Factor SP-1," PNAS 89: 9759-9763 (1992).

Kudla et al., "The Regulatory Gene Area Mediating Nitrogen Metabolite R in *Aspergillus nidulans* Mutations Affecting Specificity of Gene Activation Alter a Loop Residue of Putative Zinc Finger," EMBO J. 9(5): 1355-1364 (1990).

Laird-Offringa et al., "RNA-Binding Proteins Tamed," Nat. Structural Biol. 5(8): 665-668 (1998).

Liu et al., "Design of Polydactyl Zinc-Finger Proteins for Unique Addressing Within Complex Genomes," PNAS 94: 5525-5530 (1997).

Liu et al., "Transcription Factor EGR-1 Suppresses the Growth and Transformation of Human HT-1080 Fibrosarcoma Cells by Induction of Transforming Growth Factor Beta 1," PNAS 93(21): 11831-11836 (1996).

Liu et al., "Regulation of an Endogenous Locus Using a Panel of Designed Zinc Finger Proteins Targeted to Accessible Chromatin Regions," J Biol Chem 276:11323-11334 (2001).

Mccarty et al., "The Viviparous-1 Developmental Gene of Maize Encodes a Novel Transcriptional Activator," Cell 66:895-905 (1991).

Mandel-Gutfreund et al., "Quantitative Parameters for Amino Acid-Base Interaction: Implication for Predication of Protein-DNA Binding Sites," Nuc. Acids Res. 26(10): 2306-1312 (1998).

Margolin et al., "Kruppel-Associated Boxes Are Potent Transcriptional Repression Domains," PNAS 91: 4509-4513 (1994).

Mizushima et al., "PEF-BOS, A Powerful Mammilian Expression Vector," Nuc. Acids. Res. 18(17): 5322 (1990).

Mukhopadhyay et al., "The Von Hippel-Lindau Tumor Suppressor Gene Product Interacts With SP1 to Repress Vascular Endothelial Growth Factor Promoter Activity" Mol. Cell. Biol. 17(9): 5629-5639 (1997).

Munne-Bosch et al., "The Function of Tocopherols and Tocotrienols in Plants," Critical Reviews in Plant Sciences 21:31-57 (2002).

Nakagama et al, "Sequence and Structural Requirements for High-Affinity DNA Binding by the WT1 Gene Product," Molecular and Cellular Biology 15(3): 1489-1498 (1995).

Nardelli et al., "Zinc Finger-DNA Recognition: Analysis of Base Specificity by Site-Directed Mutagenesis," Nucleic Acids Research 20(16): 4137-4144 (1992).

Nardelli et al., "Base Sequence Discrimination by Zinc-Finger DNA-Binding Domains," Nature 349: 175-178 (1991).

Nelles et al., "Organization of the Mouse ZFHX1B Gene Encloding the Two-Handed Zinc Finger Repressor SMAD-Interacting Protein-1," Genomics 82(4):460-469 (2003).

Nekludova et al., "Distinctive DNA Conformation With Enlarged Major Groove Is Found in ZN-Finger-DNA and Other Protein-DNA Complexes," PNAS 91: 6948-6952 (1994).

Orkin et al., "Report and Recommendations of the Panel to Assess the NIH Investment in Research on Gene Therapy," (Dec. 7, 1995).

Pabo et al., "Systematic Analysis of Possible Hydrogen Bonds Between Amino Acid Side Chains and B-Form DNA," J. Biomolecular Struct. Dynamic 1: 1039-1049 (1983).

Pabo et al., Protein-DNA Recognition, Ann. Rev. Biochem. 53: 293-321 (1984).

Pabo, C.O., "Transcription Factors: Structural Families and Principles of DNA Recognition," Ann. Rev. Biochem. 61: 1053-1095 (1992).

Pavletich et al., "Crystal Structure of a Five-Finger GLI-DNA Complex: New Perspectives on Zinc Fingers," Science, 261: 1701-1707 (1993).

Pavletich et al., "Zinc Finger-DNA Recognition: Crystal Structure of a ZIF268-DNA Complex at 2.1A," Science 252: 809-817 (1991).

Pengue et al., "Repression of Transcriptional Activity at a Distance by the Evolutionarily Conserved Krab Domain Present in a Subfamily of Zinc Finger Proteins," Nuc. Acids Res. 22(15): 2908-2914 (1994).

Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," J. Virology 69(10): 6577-6580 (1995).

Pengue et al., "Kruppel-Associated Box-Mediated Repression of RNA Polymerase II Promoters is Influenced by the Arrangement of Basal Promoter Elements," PNAS 93: 1015-1020 (1996).

Pomerantz et al., "Analysis of Homeodomain Function by Structure-Based Design of a Transcription Factor," PNAS 92: 9752-9756 (1995).

Pomerantz et al., "Structure-Based Designed of a Dimeric Zinc Finger Protein," Biochemistry 37(4): 965-970 (1998).

Pomerantz et al., "Structure-Based Design of Transcription Factors," Science 267: 93-96 (1995).

Postigo et al., "C-MYB and ETS Proteins Synergize to Overcome Transcriptional Repression by ZEB," EMBO J. 16(13):3924-3934 (1997).

Postigo et al., "Differential Expression and Function of Members of the ZFH-1 Family of Zinc Finger/Homeodomain Repressors," PNAS 97(12): 6391-6396 (2000).

Qian et al., "Two-Dimensional NMR Studies of the Zinc Finger Motif: Solution Structures and Dynamics of Mutant ZFY Domains Containing Aromatic Substitutions in the Hydrophobic Core," Biochemistry 31: 7463-7476 (1992).

Quigley et al., "Complete Androgen Insensitivity Due to Deletion of Exon C of the Androgen Receptor Gene Highlights the Functional Importance of the Second Zinc Finger of the Androgen Receptor in Vivo," Molecular Endocrinology 6(7): 1103-1112 (1992).

Rauscher et al., "Binding of the WILMS' Tumor Locus Zinc Finger Protein to the EGR-I Consensus Sequence," Science 250: 1259-1262 (1990).

Ray et al., "Repressor to Activator Switch by Mutations in the First ZN Finger of the Glucocorticoid Receptor: Is Direct DNA Binding Necessary?" PNAS 88: 7086-7090 (1991).

Rebar et al., "Phage Display Methods for Selecting Zinc Finger Proteins With Novel DNA-Binding Specificities," Methods in Enzymology 267: 129-149 (1996).

Rebar et al, "Zinc Finger Phage: Affinity Selection of Fingers With New DNA-Binding Specifies," Science 263: 671-673 (1994).

Reith et al, "Cloning of the Major Histocompatibility Complex Class II Promoter Binding Protein Affected in a Hereditary Defect in Class II Gene Regulation," PNAS 86: 4200-4204 (1989).

Remacle et al., "New Mode of DNA Binding of Multi-Zinc Finger Transcription Factors: δEF1 Family Members Bind With Two Hands to Two Target Sites," EMBO J. 18(18): 5073-5084 (1999).

Rhodes et al., "Zinc Fingers: They Play a Key Part in Regulating the Activity of Genes in Many Species, From Yeast to Humans. Fewer Than 10 Years Ago No On Knew They Existed." Scientific American 268:L 56-65 (1993).

Rice et al., "Inhibitors of HIV Nucleocapsid Protein Zinc Fingers as Candidates for the Treatment of AIDS," Science 270: 1194-1197 (1995).

Rivera et al., "A Humanized System for Pharmacologic Control of Gene Expression," Nature Medicine 2(9): 1028-1032 (1996).

Rollins et al., "Role of TFIIIA Zinc Fingers in Vivo: Analysis of Single-Finger Function in Developing Xenopus Embryos," Molecular Cellular Biology 13(8): 4776-4783 (1993).

Sadowski et al., "GAL4-VP16 is an Unusually Potent Transcriptional Activator," Nature 335: 563-568 (1988).

Saleh et al., "A Novel Zinc Finger Gene on Human Chromosome 1 Qter That is Alternatively Spliced in Human Tissues and Cell Lines," American Journal of Human Genetics 52: 192-203 (1993).

Schmitz et al., "The Activation Domain of the Maize Transcription Factor Opaque-2 Resides in a Single Acidic Region," Nucleic Acids Res 25:756-763 (1997).

Shi et al., "Specific DNA-RNA Hybrid Binding by Zinc Finger Proteins," Science 268: 282-284 (1995).

Shi et al., "DNA Unwinding Induced by Zinc Finger Protein Binding," Biochemistry 35: 3845-3848 (1996).

Shi et al., "A Direct Comparison of the Properties of Natural and Designed Finger Proteins," Chem. & Biol. 2(2): 83-89 (1995).

Shintani et al., "Elevating the Vitamin E Content of Plaints Through Metabolic Engineering," Science 282: 2098-2100 (1998).

Singh et al., "Molecular Cloning of an Enhancer Binding Protein: Isolation by Screening of an Expression Library With a Recognition Site DNA," Cell 52: 415-423 (1988).

Skerka et al., "Coordinate Expression and Distinct DNA-Binding Characteristics of the Four EGR-Zinc Finger Proteins in Jurkat T Lymphocytes," Immunobiology 198: 179-191 (1997).

South et al., "The Nucleocapsid Protein Isolated From HIV-1 Particles Binds Zinc and Forms Retroviral-Type Zinc Fingers," Biochemistry 29: 7786-7789 (1990).

Spengler et al., "Regulation of Apoptosis and Cell Cycle Arrest by ZZC1, a Novel Zinc Finger Protein Expressed in the Pituitary Gland and the Brain," EMBO J. 16(10): 2814-2825 (1997).

Suzuki et al., "Stereochemical Basis of DNA Recognition by ZN Fingers," Nuc. Acids Res. 22(16): 3397-3405 (1994).

Suzuki et al., "DNA Recognition Code of Transcriptional Factors in the Helix-Turn-Helix, Probe Helix, Hormone Receptor, and Zinc Finger Families," PNAS 91: 12357-12361 (1994).

Swimoff et al, "DNA-Binding Specificity of NGFI-A and Related Zinc Finger Transcriptional Factors," Mol. Cell. Biol. 15(14): 2275-2287 (1995).

Taylor et al., "Designing Zinc-Finger ADRI Mutants With Altered Specificity of DNA Binding to T in UAS1 Sequences," Biochemistry 34: 3222-3230 (1995).

Thiesen et al., "Amino Acid Substitutions in the SP1 Zinc Finger Domain Alter the DNA Binding Affinity to Cognate SP1 Target Site," Biochem. Biophys. Res. Communications 175(1): 333-338 (1991).

Thiesen et al., "Determination of DNA Binding Specificities of Mutated Zinc Finger Domains," FEBS letters 283(1): 23-26 (1991).

Thiesen H. J. "From Repression Domains to Designer Zinc Finger Proteins: A Novel Strategy for Intracellular Immunization Against HIV," Gene Expression 5: 229-243 (1996).

Thukral et al., "Localization of a Minimal Binding Domain and Activation Regions in Yeast Regulatory Protein ADRII," Molecular Cellular Biology 9(6): 2360-2369 (1989).

Thukral et al., "Two Monomers of Yeast Transcription Factor ADRI Bind a Paldromic Sequence Symmetrically to Activate ADH2 Expression," Molecular Cellular Biol. 11(3): 1566-1577 (1991).

Thukral et al., "Mutations in the Zinc Fingers of ADRI That Change the Specificity of DNA Binding and Transactivation," Mol. Cell. Biol. 12(6): 2784-2792 (1992).

Thukral et al., "Alanine Scanning Site-Directed Mutagenesis of the Zinc Fingers of Transcriptional Factor ADRI: Residues That Contact DNA and That Transactivate," PNAS 88: 9188-9192 (1991).

Tupler et al., "Expressing the Human Genome," Nature 409:832-833 (2001).

Van Grunsven et al., "SIP1 )SMAD Interacting Protein 1) and [Delta]EF1 ([Delta]-Crystallin Enhancer Binding Factor) are Structurally Similar Transcriptional Repressors: A Current Survey of Their Functions and Mehanisms of Action in Transforming Growth Factor-[Beta] Signalling," J. Bone Joint Surgery Am. vol. 83A, Suppl 1:pp. S40-S47 (2001).

Verschueren et al., "SIP1, a Novel Zinc Finger/Homeodomain Repressor, Interacts With SMAD Proteins and Binds to 5'-CACCT Sequences in Candidate Target Genes," J. Biol. Chem. 274(29):20489-20498 (1999).

Vortkamp et al., "Identification of Optimized Target Sequences for the GL 13 Zinc Finger Protein," DNA Cell Biol. 14(7): 629-634 (1995).

Wang et al., "Dimerization of Zinc Fingers Mediated by Peptides Evolved in Vitro From Random Sequences," PNAS 96: 9568-9573 (1999).

Webster et al., "Conversion of the E1A CYS4 Zinc Finger to a Nonfunctional HIS2, CYS2 Zinc Finger by a Single Point Mutation," PNAS 88: 9989-9993 (1999).

Whyatt et al., "The Two Zinc Finger-Like Domains of GATA-1 Have Different DNA Binding Specificities," EMBO J. 12(13): 4993-5005 (1993).

Wilson et al., "In Vivo Mutational Analysis of the NGFI-A Zinc Fingers," J. Biol. Chem. 267(6): 3718-3724 (1992).

Witzgall et al., "The Kruppel-Associated Box-A (Krab-A) Domain of Zinc Finger Proteins Mediates Transcriptional Repression," PNAS 91: 4514-4518 (1994).

Wolfe et al., "Analysis of Zinc Fingers Optimized Via Phage Display: Evaluating the Utility of a Recognition Code," J. Mol. Biol. 285: 1917-1934 (1999).

Wright et al., "Expression of a Zinc Finger Gene in HTLV-I and HTLV-II Transformed Cell," Science 248:588-591 (1990).

Wu et al., "Human Immunodeficiency Virus Type 1 Nucleocapsid Protein Reduces Reverse Transcriptase Pausing at a Secondary Structure Near the Murine Leukemia Virus Polypurine Tract," J. Virol. 70(10): 7132-7142 (1996).

Wu et al., "Building Zinc Fingers by Selection: Toward a Therapeutic Application," PNAS 92: 344-348 (1995).

Yang et al., "Surface Plasmon Resonance Based Kinetic Studies of Zinc Finger-DNA Interaction," J. Immunol. Methods 183: 175-182 (1995).

Ye et al., "Engineering the Provitamin A (β-Carotene) Biosynthetic Pathway Into (Carotenoid-Free) Rice Endosperm," Science 287:303-305 (2000).

Yu et al., "A Hairpin Ribozyme Inhibits Expression of Diverse Strains of Human Immunodeficiency Virus Type 1," PNAS 90: 6340-6344 (1993).

Zhang et al., "Synthetic Zinc Finger Transcription Factor Action at an Endogenous Chromosomal Site. Activation of the Human Erythropoietin Gene," Journal of Biological Chemistry 275(43): 33850-33860 (2000).

* cited by examiner

FIGURE 1
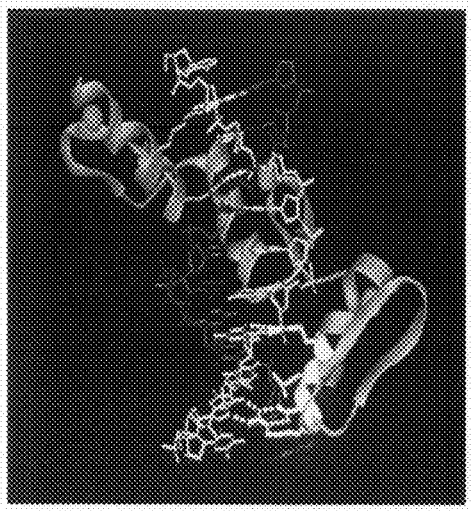
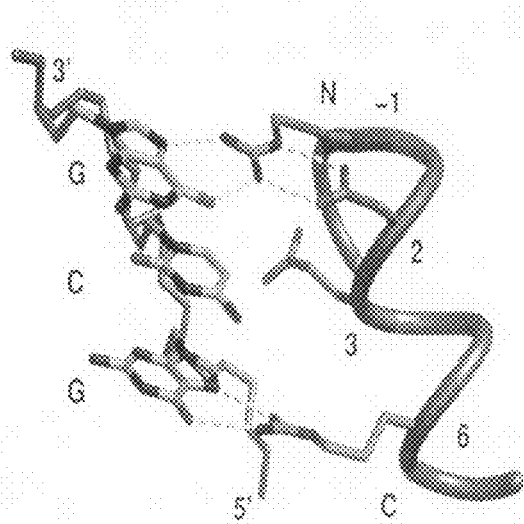
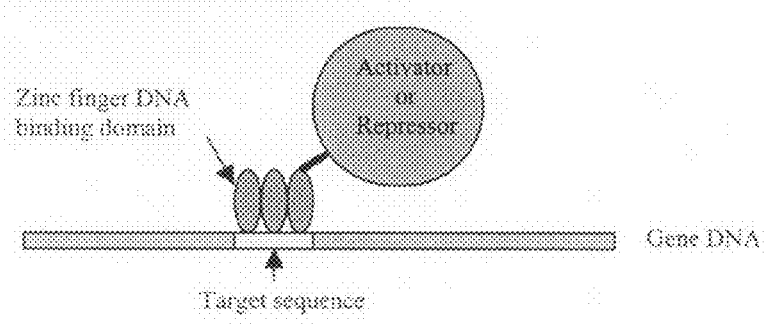

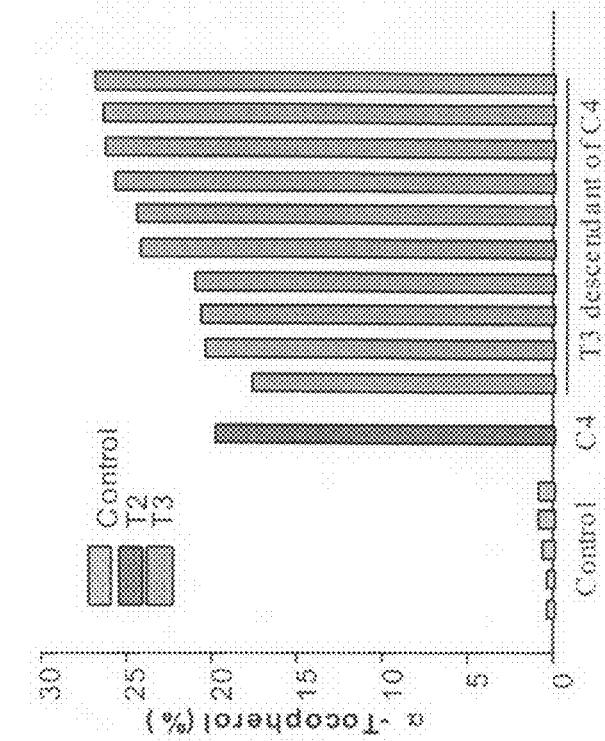
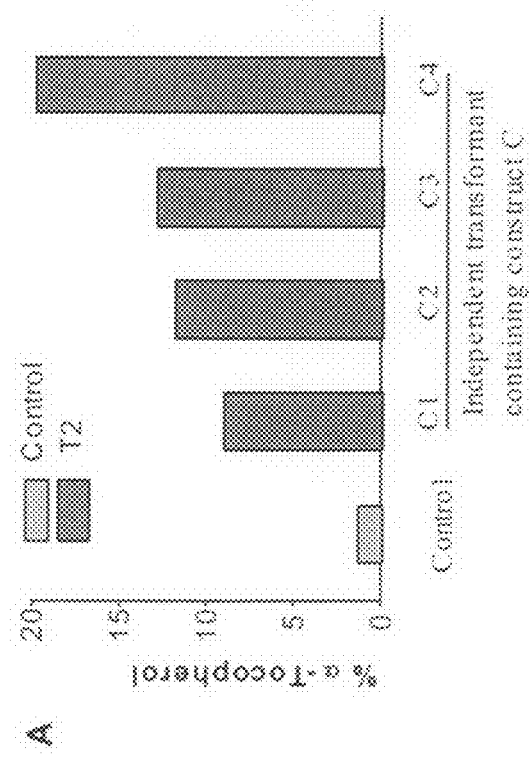
FIGURE 5

SIMULTANEOUS MODULATION OF MULTIPLE GENES

CROSS-REFERENCE TO RELATED APPLICATIONS

The present application is a divisional application of U.S. patent application Ser. No. 10/651,761, filed Aug. 29, 2003, now U.S. Pat. No. 7,361,635 which claims the benefit of U.S. Provisional Application No. 60/406,864, filed Aug. 29, 2002. The disclosures of all of the aforementioned applications are hereby incorporated by reference in their entireties for all purposes.

TECHNICAL FIELD

The present disclosure is in the field of gene regulation and the production of products.

BACKGROUND

Recombinant systems has been widely used to produce a variety of molecules including therapeutic proteins, vitamins and other dietary supplements. Plants, for example, are an extremely valuable source of essential dietary nutrients, such as vitamins. However, the expanding global human population is placing increasing strain on the ability of crop resources to meet nutrition and healthcare demands. Hence, there exists a very real need to increase production of specific molecules, for instance to increase the nutritional and economic value of crops. In addition, physiological traits that enhance a crop's growth characteristics, or its competitive edge in the face of adverse climate or pathogens, are also of economic value.

The vast majority of agronomic traits are quantitative and are controlled polygenetically. For example, the high-value nutrient α-tocopherol (vitamin E) is the end product of a complex series of chemical and enzymatic events, rather than the product of a specific gene (indeed, α-tocopherol synthesis is known to involve the action of at least 16 enzymes. See, e.g., Munne-Bosch & Alegre (2002) *Critical Reviews in Plant Sciences* 21:31-57. Genetic engineering to maximize the synthesis of such products will likely require increasing the expression of several genes central to its metabolic pathway.

At present, the commonly used technology for increasing the level of a product is the introduction of cDNA encoding the protein of interest. Overexpression of a protein that is the rate-limiting factor in a synthetic pathway may give some increase in product synthesis, but this process is limited by secondary kinetic bottlenecks. While it might be desirable to simply add further cDNAs to overcome such barriers, there are several technical limitations that render this conventional approach to multigenic engineering inappropriate when the regulation of many genes is required:

(i) The efficiency of transgene integration decreases with increasing size of the targeting construct. Thus, the insertion of several (e.g., more than 5, 8 or even 10) cDNAs and promoters into a single targeting construct would, in many cases, have a significant negative impact upon the efficiency of integration.

(ii) Inserting multiple transgenes into cell line as individual DNA constructs requires a different selection marker for each new gene. However, there is a limit to the number of different selection markers available—especially where industry/consumer concerns over the use of antibiotic markers is an issue.

(iii) There are a limited number of characterized promoters available to drive the expression of cDNAs. For instance, repeated promoter use may lead to gene silencing in plants, which do not tolerate repetitive regulatory sequences well.

(iv) Repeated transformations or cross breeding to insert all the cDNAs would be very time consuming.

In some cases it may feasible to utilize the above approach to multigenic regulation for a very limited number of genes in a pathway (two or three at most). Indeed, this approach has been used successfully to increase the level of β-carotene (the precursor to vitamin A) in rice. See, e.g., Ye, X. et al. (2000) *Science* 287:303-5.

Thus, when faced with the challenge of simultaneously regulating many (e.g., ten or even more) genes in order to maximize the level of production, existing technologies fall well short of delivering this capability.

Therefore, there remains a need for compositions and methods for overexpressing multiple genes in a target cell or organism. Such methods would open up vast new economic opportunities, for example in agronomy.

BRIEF DESCRIPTION OF THE FIGURES

FIG. 1, panel A, shows the crystal structure of Zif268 (which contains three linked zinc fingers) bound to double-stranded DNA. The critical residues for basepair recognition are the whitest residues in the bottom right hand-corner.

FIG. 1, panel B, depicts a close-up representation of residues important for basepair contacts in one of the fingers. These residues are generally changed to create engineered proteins that recognize specific, selected sites;

FIG. 1, panel C, is a schematic showing a zinc finger DNA binding domain linked to a transcription regulatory domain (Activator or Repressor), bound to a specific DNA sequence in the target gene. (A three-finger module—schematically shown here recognizes a 9 basepair target site).

FIG. 2, panel B, depicts DNA recognition by the two zinc finger master libraries, Lib12 and Lib23. The libraries are based on the three-finger DNA-binding domain of Zif268 and the binding scheme is based on the crystal structure of the wild-type domain in complex with DNA. The DNA-binding positions of each zinc finger are numbered and randomized residues in the two libraries are circled. Broken arrows denote possible DNA contacts from Lib12 to bases H'IJKLM and from Lib23 to bases MNOPQ. Solid arrows show DNA contacts from those regions of the two libraries that carry the wild-type Zif268 amino acid sequence, as observed in the crystal structure. The wild-type portion of each library target site (white boxes) determines the register of the zinc finger-DNA interactions. As explained herein, Lib12 gives two-finger modules that recognize sites of the form 5'-GNNNNN-3' and Lib23 gives two-finger modules that recognize sites of the form 5'-NNNNNG-3'.

FIG. 4, panel B, shows DNase I hypersensitivity mapping of the *Arabidopsis* GMT gene. Four vertical bars indicate the four hypersensitive sites.

FIG. 4, panel C, shows differential activation of the *Arabidopsis* GMT gene by 6 ZFP-TFs (A-F) targeted to different sites on the GMT locus. Cont=the transcription activation domain C1 expressed without a ZFP DNA binding domain attached.

FIG. 5, panel A, is a graph depicting levels of α-tocopherol in T2 and T3 seeds in *Arabidopsis* transformed with ZFP-TF "C". The proportion of tocopherol expressed as a percentage of total tocopherols in T2 seeds. C1 to C4 are T2 seeds from four independent T1 plants that contain ZFP "C". Control is T2 seeds from control plants transformed with an empty transformation vector.

FIG. 5, panel B, is a graph depicting tocopherol levels in T3 seeds. The five left-most bars show control levels. The sixth bar (C4) from the left represents α-tocopherol level (as percentage of total tocopherols) in the C4 T2 seeds. The 10 right-most bars (gray) represent α-tocopherol percentages in T3 seeds from different T2 plants expressing C4.

SUMMARY

Figure 2:
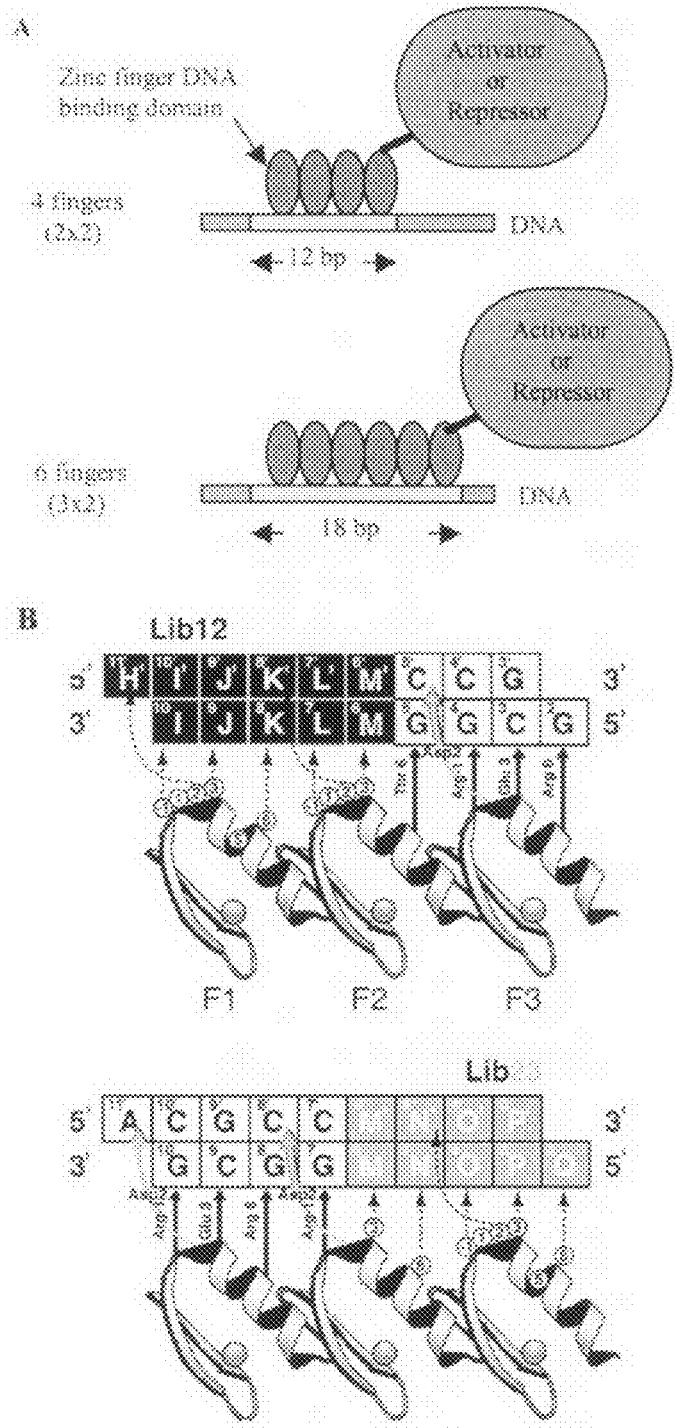
FIG. 2, panel A, shows composition of the 'bipartite' library. In particular, individual "2-zinc-finger" units that recognize 5'-GNNNNN-3' or 5'-NNNNNG-3' hexamers can be linked together to form 4-finger or 6-finger ZFPs that recognize 12 or 18 basepairs of DNA, respectively. The zinc finger proteins described herein can target either strand and, in addition, the spacing between two-finger modules can be adjusted. Accordingly, an occasional guanine may be present. An 18 basepair site typically is large enough that it represents a unique site in the human genome.

The present disclosure overcomes the problems inherent in multigenic regulation, by simultaneously modulating (e.g., upregulating and/or downregulating) the expression of essentially some or all of the key enzymes within a specific metabolic pathway using a single transgene deliverable. The basis of our approach is to engineer a single customized zinc finger protein transcription factor (ZFP-TF) that will bind to and modulate expression of an entire set of endogenous genes (i.e., genes in their normal chromosomal context) that are specific for the target pathway.

In certain embodiments, a multi zinc finger protein is provided comprising two or more engineered zinc finger proteins, wherein the multi zinc finger protein modulates expression of two or more endogenous genes (e.g., three or more genes, five or more genes, eight or more genes, or even ten or more genes). Each zinc finger protein can comprise at least two zinc finger modules, for example a zinc finger module that binds to a 3 base pair subsite in target site of the endogenous gene. The zinc finger proteins can be linked together using linker molecules as described in the art. In certain embodiments, the multi zinc finger proteins further comprise at least one functional domain (e.g., activation and/or repression domain), for example a functional domain for each zinc finger protein. Any of the multi zinc finger proteins described herein can be included in a composition, for example a pharmaceutical composition comprising one or more pharmaceutically acceptable excipients.

In certain aspects, the endogenous genes targeted by the multi zinc finger proteins are involved in a metabolic pathway, for example, synthesis of a product. In certain embodiments, the endogenous genes are plant genes, for example genes involved in tocopherol synthesis.

Any of the multi zinc finger proteins described herein may be encoded by one or more nucleic acid molecules.

In other embodiments, any of the compositions described in herein can be used in methods of modulating the level of a product in a eukaryotic cell, comprising contacting the eukaryotic cell with any of the compositions disclosed herein, under conditions such that levels of the product are modulated.

These and other embodiments will readily occur to those of skill in the art in light of the disclosure herein.

DETAILED DESCRIPTION

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Third Edition, Cold Spring Harbor Laboratory Press, 2001; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

DEFINITIONS

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues.

The term also applies to amino acid polymers in which one or more amino acids are chemical analogues or modified derivatives of a corresponding naturally occurring amino acid, for example selenocysteine (Bock et al. (1991) *Trends Biochem. Sci.* 16:463-467; Nasim et al. (2000) *J. Biol. Chem.* 275:14, 846-14,852) and the like.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. A "binding profile" refers to a plurality of target sequences that are recognized and bound by a particular binding protein. For example, a binding profile can be determined by contacting a binding protein with a population of randomized target sequences to identify a sub-population of target sequences bound by that particular binding protein.

A "zinc finger binding protein" is a protein or segment within a larger protein that binds DNA, RNA and/or protein in a sequence-specific manner as a result of stabilization of protein structure through coordination of a zinc ion. The term zinc finger binding protein is often abbreviated as zinc finger protein or ZFP. A "canonical" zinc finger refers to a zinc-coordinating component (e.g., zinc finger) of a zinc finger protein having the general amino acid sequence: Cys-$X_{2-4}$-Cys-$X_{12}$-His-$X_{1-7}$-His (SEQ ID NO:1) where X is any amino acid (also known as a C2H2 zinc finger). A "non-canonical" zinc finger refers to any type of finger other than a C2H2 zinc finger. Examples of non-canonical zinc fingers are described in co-owned U.S. Patent Application Publication No. 2003-0108880 (Jun. 12, 2003).

A "designed" zinc finger protein is a protein not occurring in nature whose structure and composition results principally from rational criteria. Criteria for rational design include application of substitution rules and computerized algorithms for processing information in a database storing information of existing ZFP designs and binding data, for example as described in co-owned PCT WO 00/42219. A "selected" zinc finger protein is a protein not found in nature whose production results primarily from an empirical process such as phage display, two-hybrid systems and/or interaction trap assays. See e.g., U.S. Pat. No. 5,789,538; U.S. Pat. No. 6,007,988; U.S. Pat. No. 6,013,453; WO 95/19431; WO 96/06166; WO 98/54311 and Joung et al. (2000) *Proc. Natl. Acad. Sci. USA* 97:7382-7387. Selection methods also include ribosome display systems (e.g., PCT WO 00/27878) and mRNA-peptide fusion systems (e.g., U.S. Pat. No. 6,207,446; PCT WO 00/47775). Amino acid sequences of polypeptides (e.g., zinc fingers) obtained by selection or design are referred to as "adapted" amino acid sequences. Designed and/or selected ZFPs are modified according to the methods and compositions disclosed herein and may also be referred to as "engineered" ZFPs.

The term "naturally-occurring" is used to describe an object that can be found in nature, as distinct from being artificially produced by a human.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the term "operatively linked" can refer to the fact that each of the components performs the same function in linkage to the other component as it would if it were not so linked. For example, with respect to a fusion polypeptide in which an engineered ZFP DNA-binding domain is fused to a functional domain (or functional fragment thereof), the ZFP DNA-binding domain and the functional domain (or functional fragment thereof) are in operative linkage if, in the fusion polypeptide, the ZFP DNA-binding domain portion is able to bind its target site and/or its binding site, while the functional domain (or functional fragment thereof) is able to modulate (e.g., activate or repress) transcription.

"Specific binding" between, for example, a ZFP and a specific target site means a binding affinity of at least $1 \times 10^6$ $M^{-1}$.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion and fusion nucleic acids (for example, a nucleic acid encoding the fusion polypeptides described herein). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see below), as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of an mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the engineered zinc finger-nucleotide binding polypeptides disclosed herein can modulate the activity of two or more promoter sequences by binding to a motif within the promoters, thereby inducing, enhancing or suppressing transcription of a gene operatively linked to the promoter sequences. Alternatively, modulation may include inhibition of transcription of one or more genes wherein the zinc finger-nucleotide binding polypeptide binds to the structural gene and blocks DNA dependent RNA polymerase from reading through the gene, thus inhibiting transcription of the gene. Alternatively, modulation may include inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) *Nature Biotechnology* 15:961-964); changes in signal transduction; changes in phosphorylation and dephosphorylation; changes in receptor-ligand interactions; changes in concentrations of second messengers such as, for example, cGMP, cAMP, $IP_3$, and $Ca2^+$; changes in cell growth, changes in chemical composition (e.g., nutritional value), and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

"Eucaryotic cells" include, but are not limited to, fungal cells (such as yeast), plant cells, animal cells, mammalian cells and human cells. Similarly, "prokaryotic cells' include, but are not limited to, bacteria.

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a ZFP to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340: 245-246; U.S. Pat. No. 5,585,245 and PCT WO 98/44350.

A "target site" or "target sequence" is a sequence that is bound by a binding protein such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

The term "effective amount" includes that amount which results in the desired result, for example, deactivation of a previously activated gene, activation of a previously repressed gene, or inhibition of transcription of a structural gene or translation of RNA.

As used herein, "plant" refers to either a whole plant, a plant tissue, a plant part, such as pollen, seed or an embryo, a plant cell, or a group of plant cells. The class of plants that can be used is generally as broad as the class of seed-bearing higher plants amenable to transformation techniques, including both monocotyledonous and dicotyledonous plants. Seeds derived from plants regenerated from transformed plant cells, plant parts or plant tissues, or progeny derived from the regenerated transformed plants, may be used directly as feed or food, or can be altered by further processing. In the practice of the present disclosure, the most preferred plant seeds are those of *Arabidopsis* and *Brassica*. The transformation of the plants may be carried out in essentially any of the various ways known to those skilled in the art of plant molecular biology. These include, but are not limited to, microprojectile bombardment, microinjection, vacuum infiltration, electroporation of protoplasts or cells comprising partial cell walls, and *Agrobacterium*-mediated DNA transfer.

DETAILED DESCRIPTION

The regulation of gene expression is one of the most fundamental processes in all of biology. Gene expression is normally controlled by the concerted action of transcription factors that bind to and regulate gene promoter activity at various chromosomal sites. These transcription factors typically bind to DNA elements located within regulatory regions of genes, and they can induce the activation or repression of gene expression. Transcription factors generally contain both (i) a DNA binding domain (e.g., to target the protein to a specific site in the genome) and (ii) a regulatory domain (e.g., signals whether the genes near this binding site should be turned on or turned off).

The capacity to engineer transcription factors that bind to and regulate the expression of endogenous genes, thereby tapping into the normal physiological mechanisms of gene control has been described, for example in WO/0183819 and WO/0119981 and the references cited therein. Briefly, this technology involves the engineering of artificial transcription factors (containing both DNA-binding and transcription-regulation domains) that can bind to any desired site in the genome. These transcription factors can be transiently or stably expressed within a plant or animal cell and thus, this strategy is an immensely powerful approach for controlling individual gene expression. To date, this technology has been applied to selectively target one gene per engineered transcription factor. The transition from single-gene to multi-gene regulation represents an enormous technical challenge but has incredibly exciting implications. Our approach uses designed transcription factors that have a zinc finger DNA binding domain (ZFPs), for example of the $Cys_2$-$His_2$ class. See, e.g., Tupler et al. (2001) *Nature* 409:832-3.

Design and selection studies have demonstrated the amazing versatility of this motif, and powerful strategies for the design of ZFPs (that contain, for example, 3, 4, or 6 fingers) that can recognize virtually any desired DNA sequence (of 9, 12 or 18 basepairs, respectively) have been developed. See, e.g., Jamieson et al. (1994) *Biochemistry* 33:5689-95; Rebar & Pabo (1994) *Science* 263:671-3; Rebar et al. (1996) *Methods Enzymol* 267:129-49; Desjarlais & Berg (1992) *Proc Natl Acad Sci USA* 89:7345-9; Greisman & Pabo (1997) *Science* 275: 657-61; Choo & Klug (1994) *Proc Natl Acad Sci USA* 91:11163-7.

Each individual finger in a $Cys_2$-$His_2$ zinc finger protein contains an α-helix (FIG. 1a). The aminoterminal region of each α-helix contains four amino acid residue positions that are especially critical for making specific base pair contacts, and each finger contacts a 3-4 base pair region along the DNA (FIG. 1b). See, e.g., Jamieson et al. (1994) *Biochemistry* 33:5689-95. By varying the residues used at these key positions, the DNA-binding specificity of each individual finger can be altered to recognize the desired 3-4 basepair region. Therefore, the DNA binding domain of each engineered transcription factor contains a set of linked fingers that recognizes a specific site in the target gene promoter. However, DNA binding per se generally may not be sufficient to regulate transcription. In such instances, we attach appropriate transcription activation or repression domains to zinc finger proteins to produce artificial zinc finger protein transcription factors (ZFP-TFs) that will (by virtue of the specificity inherent in the DNA-binding domain) be able to turn on or turn off any endogenous gene (FIG. 1c).

A central step in designing these novel transcription factors involves creating zinc finger DNA binding units that are precisely targeted to the desired DNA sequence and thus will specifically regulate the genes of interest. Phage display libraries of zinc fingers can be used to select individual zinc fingers with desired DNA-binding specificities. See, e.g., Jameison et al (1994) *Biochemistry* 33:5689-95; Rebar & Pabo, supra; Greisman & Pabo, supra; Choo et al. (1994) *Nature* 372:642-5; Isalan et al. (1998) *Biochemistry* 37:12026-33; and Isalan & Choo (2000) *J Mol Biol* 295:471-7. Selection process is typically done using a library of "two-finger" modules—that can recognize any desired six-base pair site in duplex DNA. By linking together such two-finger units, four-finger or six-finger proteins that recognize twelve-base pair or eighteen-base pair target sites, respectively, can be rapidly assembled. Recognition sites of this size will typically be large enough such that they occur only once in the human genome, thus conferring specificity of gene targeting. Details of our sequence-specific zinc finger protein selection strategy are given in Example 8 and FIG. 2.

Figure 3:
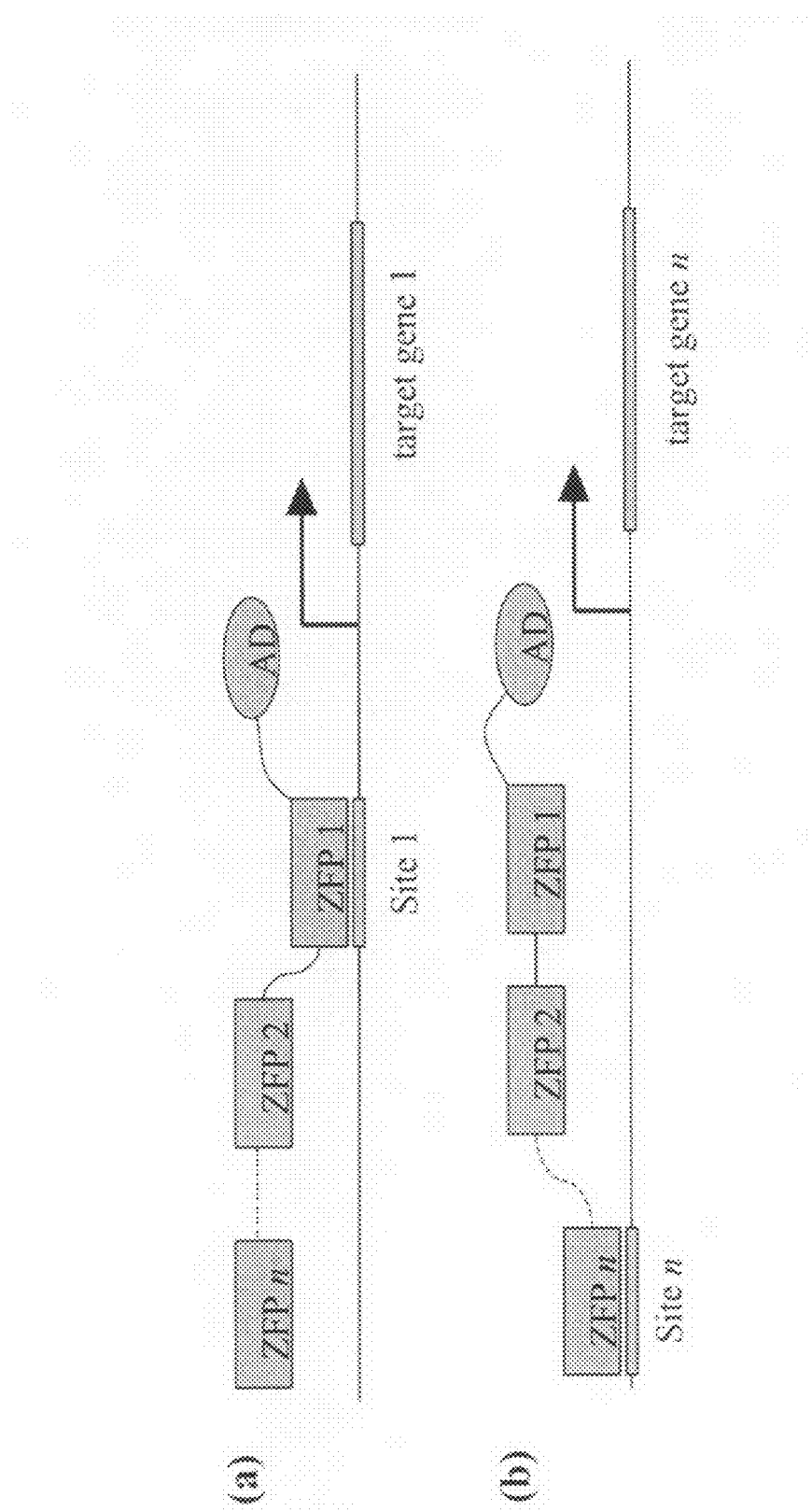
FIG. 3 depicts multiple ZFPs (ZFP1, ZFP2, ... ZFPn) that recognize sites in different target genes (gene 1, gene 2, ... gene n) are linked together, then attached to a transcription activation domain, AD.

The disclosure herein relates to a novel approach in which multiple autonomous ZFP DNA binding domains are joined by linker peptides to create a single "multiZFP" that can selectively bind to each of the genes for which it contains the cognate ZFP module (FIG. 3). In addition, a transcription regulatory domain can be added, for example to generate a functional multiZFP-TF that would simultaneously bind to and regulate each and all of the cognate target genes.

Currently, ZFP-TF approaches typically employ a single ZFP that recognizes a select 9-18 basepair sequence within the promoter of a target gene. Disclosed herein are compositions and methods involving a single ZFP-TF that simultaneously regulates several key genes, for example multiple genes in a biosynthetic pathway is engineered. Thus, a single multiZFP-TF as disclosed herein binds to several individual gene promoters, for example several genes within a synthesis pathway.

Further, the ZFPs described herein are preferably highly effective on each target gene to which they bind. As described herein, each ZFP-TF typically comprises two domains: a DNA binding domain, and a transcription regulatory domain (activator or repressor). Thus, binding function may be separate from regulatory function. The transcription regulatory function of that ZFP-TF is determined, in part, by the local chromatin environment and the presence of adjacent transcription factors and, accordingly, different regulatory domains may exhibit promoter context-dependent efficacy (e.g., one type of activation domain might be more effective on promoter A than on promoter B, while the converse may apply for a different activation domain). Thus, in the context of the present disclosure it is preferred that the ZFP-TF not only bind to all the selected target genes, but also retain the capacity to effectively modulate transcription from all of those genes.

This disclosure represents a significant improvement over current technologies by providing the ability to generate a single multiZFP-TF that modulates more than one target gene. For example, in the context of dietary supplements, administration of such multiZFPs (e.g., via insertion into the plant genome), will activate the major rate limiting genes in the α-tocopherol synthesis pathway and result in a dramatic increase in the level of α-tocopherol in the seed oil of the plant.

Table 1 illustrates some of the differences between the disclosure presented herein and other methods.

malian systems. Transgenic regulation of synthesis pathways in humans have great potential in medicine and healthcare. In addition, application of such a technology to animals could enhance the nutritional value of meat or milk products, with obvious economic rewards.

Further, while the following examples describe activation of key target genes, it should be noted that the present disclosure is equally applicable to designing and using multiZFPs that repress gene expression. For example, targeted gene repression using multiZFP-TFs to shut down pathways can be used to repress proteins that may otherwise result in the turnover of valuable metabolites, thereby too increasing the level of economically valuable products.

All references cited herein are hereby incorporated by reference in their entirety for all purposes.

The following examples are presented as illustrative of, but not limiting, the claimed subject matter.

EXAMPLES

We have recently demonstrated the efficacy of targeted gene regulation in plants using engineered ZFP-TFs, including several genes in *Arabidopsis*, canola and soybean. In *Arabidopsis* >95% of total tocopherols exist as γ-tocopherol—the precursor to α-tocopherol. The enzyme γ-tocopherol methyltransferase (GMT) is responsible for the conversion of γ-tocopherol into α-tocopherol in the terminal step of α-tocopherol synthesis. A recent study has shown that overexpression of the cDNA encoding GMT in *Arabidopsis* gave >80-fold increase in the level of seed α-tocopherol, such that α-tocopherol represented >95% of total tocopherols. See, e.g., Shintani et al. (1998) *Science* 282:2098-2100. Data presented herein demonstrate activation of the gene encoding γ-tocopherol methyltransferase (GMT) in *Arabidopsis* using a ZFP-TF containing the maize C1 transcription activation domain. See, e.g., Goff et al. (1991) *Genes Dev* 5:298-309. By targeting ZFP-TFs to accessible regions of the promoter of

TABLE 1

| | | Variables | | |
|---|---|---|---|---|
| variable | Technical Targets | Current Practice | Associated Barriers | Innovative Approach |
| Multigenic regulation (e.g., biosynthetic pathway) | 3-fold increase in expression of up to 8 genes simultaneously | Activation of 1-2 genes only using cDNA | Insertion of multiple cDNA transgenes | Switch on multiple key endogenous genes using only one transgenic factor. |
| Total protein synthesis | 3-fold increase | Non-existent | Activating all key rate-limiting steps in synthesis simultaneously | Customize a single transgenic factor to selectively activate all key endogenous genes |

Figure 4:
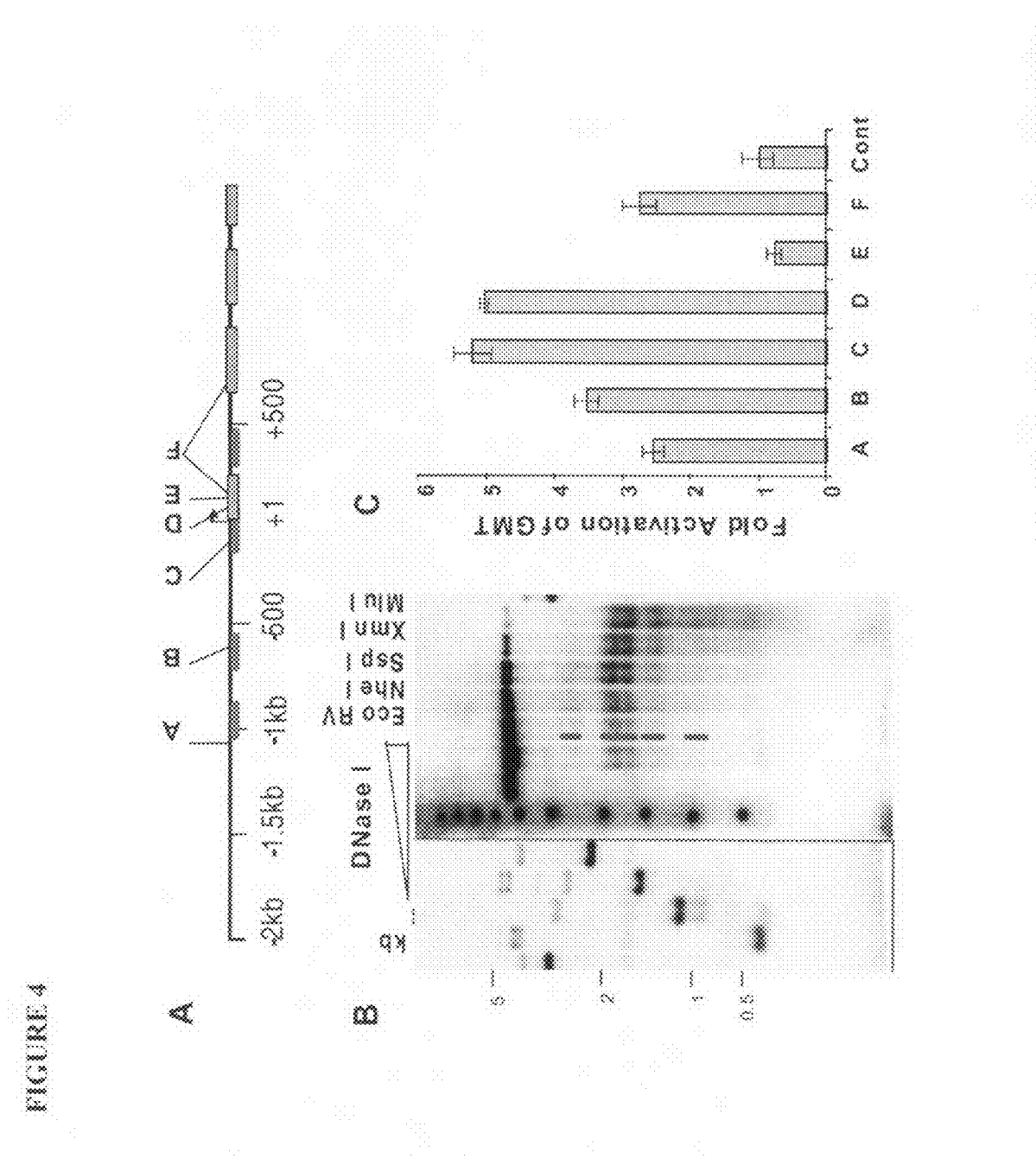
FIG. 4, panel A, depicts *Arabidopsis* GMT gene structure. Transcription start site (+1), the four exon regions of the GMT gene (fourth, sixth, seventh and eighth rectangles), the location of the target sites of six ZFPs as well as the four DNase I hypersensitive sites (first, second, third and fifth rectangles) are shown.

While the foregoing is applicable to genes in any organism, the disclosure is exemplified herein by showing production of tocopherol in *Arabidopsis*. The successful development of these systems will have a much larger impact on protein production and particularly agronomy in general. Thus, this technology could be broadly applied to increase the level of any high value product in any organism. Enhancing the level of these products in primary sources (e.g., as plants) will likely have a significant impact on the efficacy of downstream harvesting and extraction technologies. Furthermore, because the principles of gene regulation are conserved throughout eukarya, plant studies exemplified herein are directly applicable to the transfer of this technology to mam- GMT in *Arabidopsis*, as determined by DNAseI hypersensitivity mapping (FIGS. 4a&b), we were able to activate GMT expression by 5-fold (FIG. 4c). The proportion of α-tocopherol was increased from 1% to approximately 27% of total tocopherols (27-fold) in the T3 seed oil of T2 plants transgenic for individual ZFP-TFs (FIGS. 5a&b). See, also, Shintani et al. (1998) *Science* 282:2098-2100. Based on the above report, optimization of the ZFP-TF will likely also achieve near-complete conversion of the γ-tocopherol. In a parallel study, canola GMT was upregulated by a similar approach and the proportion of α-tocopherol was increased from about 30% to approximately 90% of total tocopherols. Thus, the use of engineered ZFP-TFs is an effective method for controlling individual gene expression in plants.

Example 1

α-Tocopherol Synthesis as a Model System for Multigenic Regulation

The studies summarized above demonstrate that the potential for further increasing α-tocopherol synthesis is limited by the level of total tocopherol (in particular, γ-tocopherol) synthesized prior to the final GMT-mediated step. Hence, substantially increasing total tocopherol synthesis would provide even greater potential for the activated GMT to then convert this to high levels of α-tocopherol. This pathway (summarized in FIG. 6) has been well characterized by others and a wealth of information is available on the enzymes that mediate key intermediate steps. See, e.g., Keller et al. (1998) *European Journal of Biochemistry* 251:413-417. Furthermore, the *Arabidopsis* sequencing project has provided the sequence of most genes in the tocopherol pathway, for example, the *Brassica* GMT sequence is disclosed in WO 02/063022. Thus, tocopherol synthesis in *Arabidopsis* provides an ideal model system for multigenic regulation within a defined metabolic pathway and demonstrates that is applicable to virtually any polygenetic trait (e.g., in any organism).

Example 2

Assaying for ZFP-TF Efficacy

ZFP-TF efficacy is assessed as follows. Initial ZFP-TF efficacy in the activation of gene expression is determined by transiently transfecting the ZFP-TF (or multiZFP-TF) DNA into *Arabidopsis* leaf protoplasts. mRNA expression from the target gene is measured after 18 hours using RT-PC, verifying that the ZFP-TFs effectively regulate the desired target genes.

To examine the effect of each ZFP-TF (or multiZFP-TF) on the total tocopherol level in seed oil, those ZFPs that have been validated for their capacity to activate individual gene expression in protoplasts are stably transformed into *Arabidopsis* using the "floral dip" method. T2 seeds are collected from mature plants and analyzed (by external contractor) with respect to the level of total tocopherols—including α-tocopherol—and key intermediates in the tocopherol synthesis pathway.

Example 3

Effect of ZFP Number on MultiZFP-TF Stability and Function

Figure 7:
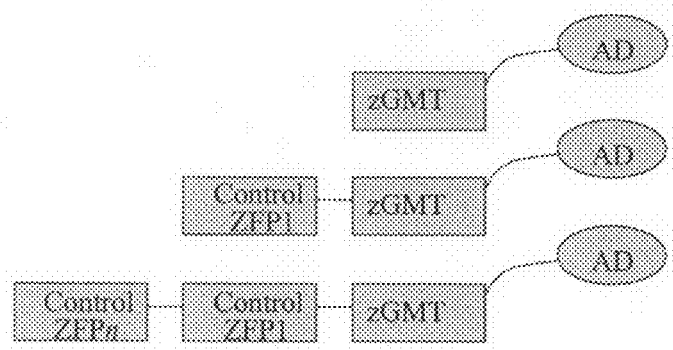
FIG. 7 depicts the effect of additional ZFPs on multiZFP stability and function. Additional ZFPs (ZFP1 . . . ZFPn) are added to the N-terminus of the GMT-activating ZFP-TF (zGMT) and the expression, stability, and functionality of the resulting zGMT assessed.

The affect on the stability and functionality of additional ZFPs, when linked to an existing functional ZFP-TF is evaluated. Earlier GMT activation studies showed that the most effective ZFP-TF contained a ZFP linked to the *Arabidopsis* C1 activation domain (See, FIGS. 4&5). This ZFP-TF is designated "zGMT." To study the effects of adding multiple ZFPs to a ZFP-TF on that ZFP-TF's expression and DNA binding, a series of modifications of zGMT in which up to seven control ZFPs (that do not bind to any sites in the GMT promoter) are attached to the N-terminal end of zGMT (giving a maximum total of eight ZFPs within a multiZFP-TF). The C1 activation domain remain attached directly to the C-terminus of the GMT-specific ZFP (FIG. 7). These multiZFP-TFs are transfected into *Arabidopsis* protoplasts.

To assess the expression and stability of the multiZFP-TF, the mRNA and protein levels for each of the constructs are assayed by RT-PCR and Western blot analysis, respectively. If the multiZFP-TF mRNA levels are significantly lower that zGMT alone, the multiZFP gene is likely being silenced, for example, due to excessive repetitive DNA sequence. In this event, silencing may be overcome by changing the codon usage in the gene encoding the multiZFP-TF. If low multiZFP-TF protein expression is occurring, but the mRNA level is similar to zGMT, the protein itself is likely being rapidly degraded, or that translation efficiency has been affected. In such cases, (i) a different zinc finger backbone sequence may be used and/or (ii) the linker sequence between adjacent ZFPs may be changed. However, even if multiZFP-TF protein expression appears normal, there is no guarantee that it will be authentically folded. The increased size of the multiZFP-TFs, compared with single gene ZFP-TFs, may hinder protein folding and/or reduce solubility. If in vivo function analyses of the multiZFP-TFs (with respect to GMT activation) show unexpectedly poor activity, Western blot comparison of the soluble fraction of plant cells with the insoluble fraction is used to determine whether this lack of activity is due to poor solubility. Further, gel mobility shift assays quantitated by Scatchard analysis are used to measure the effective DNA binding affinity and the level of functionally active multiZFP-TF molecules (with respect to DNA binding).

Even if a multiZFP-TF is efficiently expressed, its efficacy could be affected by several parameters, including intramolecular interference of DNA binding by the multiple ZFPs, and impaired function of the activation domains. In a previous study, we demonstrated that connecting two ZFPs with flexible linker peptides does not significantly affect the DNA binding affinity of either ZFP. See, e.g., Kim & Pabo (1998) *Proc Natl Acad Sci USA* 95:2812-7. However, in the present scenario this consideration is extended to a larger number of linked ZFPs and thus, potentially more complex inter-ZFP relationships.

To determine the effects of the ZFP extension on the transcription mechanism per se, the level of GMT expression (the target gene) is analyzed (in addition to that of the multiZFP-TF). Typically, GMT activation using multiZFP-TFs is >50% as effective as using zGMT alone. If the desired level of activity is not achieved with the multiZFP-TF containing up to 8 ZFP moieties, then the maximum number of ZFP extensions is reduced (assuming this will concomitantly increase efficacy).

Thus, efficient simultaneous activation of at least four genes is achieved using a single multiZFP-TF.

Example 4

Effect of Activation Domain Position

Figure 8:
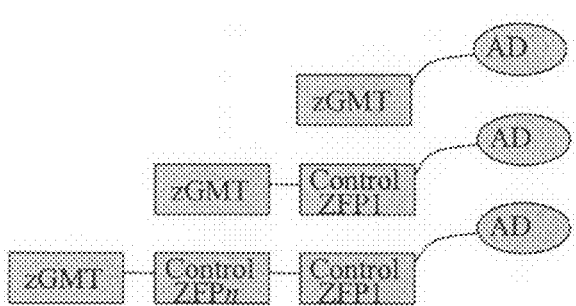
FIG. 8 depicts the effect of distance of separation from the DNA-binding ZFP on activation domain function. The activation domain (AD) is tethered directly to the DNA-binding ZFP (zGMT), or separated from it by up to n ZFPs.

To examine the issue of activation domain position, the GMT-specific ZFP with multiple control ZFPs linked to it is used. However, instead of linking the C1 activation domain directly to the GMT-specific ZFP, it is linked to the most distal control ZFP in a series of extensions to zGMT (up to 7 additional ZFPs; FIG. 8). We require that GMT activation using each multiZFP-TF containing a distal C1 domain is >50% as effective as using zGMT alone.

Figure 9:
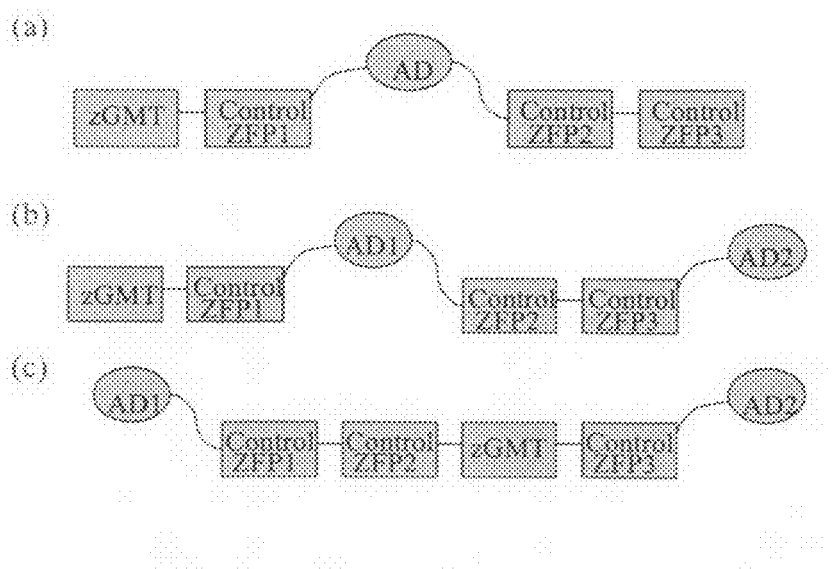
FIG. 9 depicts different potential structures for multiZFPs. (a) The activation domain (AD) lies internal to the string of ZFPs; (b) Multiple AD within the same multiZFP; (c) Surrounding the DNA-binding ZFP (on both sides) with other ZFP or AD structures.

If the above studies reveal that distancing the activation domain from the point of DNA binding is detrimental to multiZFP-TF function, then the value of inserting the activation domains within the chain of ZFPs linked to zGMT (FIG. 9a) is examined, thereby decreasing the distance to the farthest ZFP and so may have a positive influence on multiZFP- TF activity. To extend this approach one step further, the value of inserting multiple activation domains throughout the multiZFP-TF is tested (FIG. 9b).

Finally, position effects of the DNA binding ZFP itself are examined. All the experiments described above place the zGMT at either the N- or C-terminus of the multiZFP-TF. The efficacy of the multiZFP-TF when the tethering ZFP is located in the middle of the string of ZFPs (FIG. 9c) is examined, as will be the case for all but the terminal ZFPs in any final multiZFP-TF. The criteria for success are that the multiZFP-TF contains at least four ZFPs and achieves >50% of the activity attained by zGMT—irrespective of the position of the tethering ZFP.

Thus, the optimal position of the regulatory (e.g., activation) domain is determined.

Example 5

Activation of Individual Genes in the Tocopherol Synthesis Pathway

A series of individual ZFP-TFs that bind to and regulate each of 15 individual target genes identified in the tocopherol synthesis pathway (FIG. 6) are developed using the following methods. See, also, Example 4.

First, regions of the target gene promoters that are accessible to ZFP-TF binding are identified. As shown in FIG. 4b, DNaseI hypersensitivity mapping is used in *Arabidopsis* leaf tissue to identify regions of open chromatin structure in the target promoters. These regions usually coincide with critical "regulatory" regions within the promoter of a gene that are important for controlling the gene's expression. Thus, the effectiveness of our ZFP-TFs by targeting them to these regions is maximized. See, e.g., Liu et al. (2001) *J Biol Chem* 276:11323-34; Zhang et al. (2000) *J Biol Chem* 275:33850-60.

Second, the ZFP-TFs are designed that bind specifically to sites within the DNAseI hypersensitive sites in each target gene promoter using our library of over 500 2-finger ZFP modules (described earlier, and in Example 8 and FIG. 2), each of which has known specificity for a different 6-7 basepair DNA sequence, and combine these modules to generate 4-finger ZFPs that specifically recognize 12 basepair sequences in the accessible regions of the target gene promoters. These ZFPs are linked to the transcriptional activator domain C1 to generate a series of complete ZFP-TFs. Thus, approximately 10 ZFP-TFs for each target gene are generated.

Subsequently, ZFP-TFs for activation of target genes are screened. Each ZFP-TF generated is transfected into *Arabidopsis* protoplasts and the level of expression of each target gene in the presence of each ZFP-TF measured by RT-PCR (and compared with control cells transfected with a vector containing the C1 activation domain, but no DNA binding domain). ZFP-TFs that achieve >4-fold activation of expression above control levels for each target gene are identified.

Example 6

Design of a MultiZFP-TF to Activate Tocopherol Synthesis

Two or more ZFP-TFs are combined into one multiZFP-TF using the results obtained regarding distribution of ZFPs and activation domains throughout the multiZFP-TF.

The multiZFP-TF are constructed by linking two or more individual ZFPs together. The multiZFP may include all of the individual ZFPs and thereby simultaneously target all the genes of the tocopherol pathway. Alternatively, only the ZFPs that target genes having the greatest influence on tocopherol synthesis (as determined above), are linked to form a multiZFP. Without being bound by one theory, suitable target genes may occur near the end of the pathway (see FIG. 6).

Figure 6:
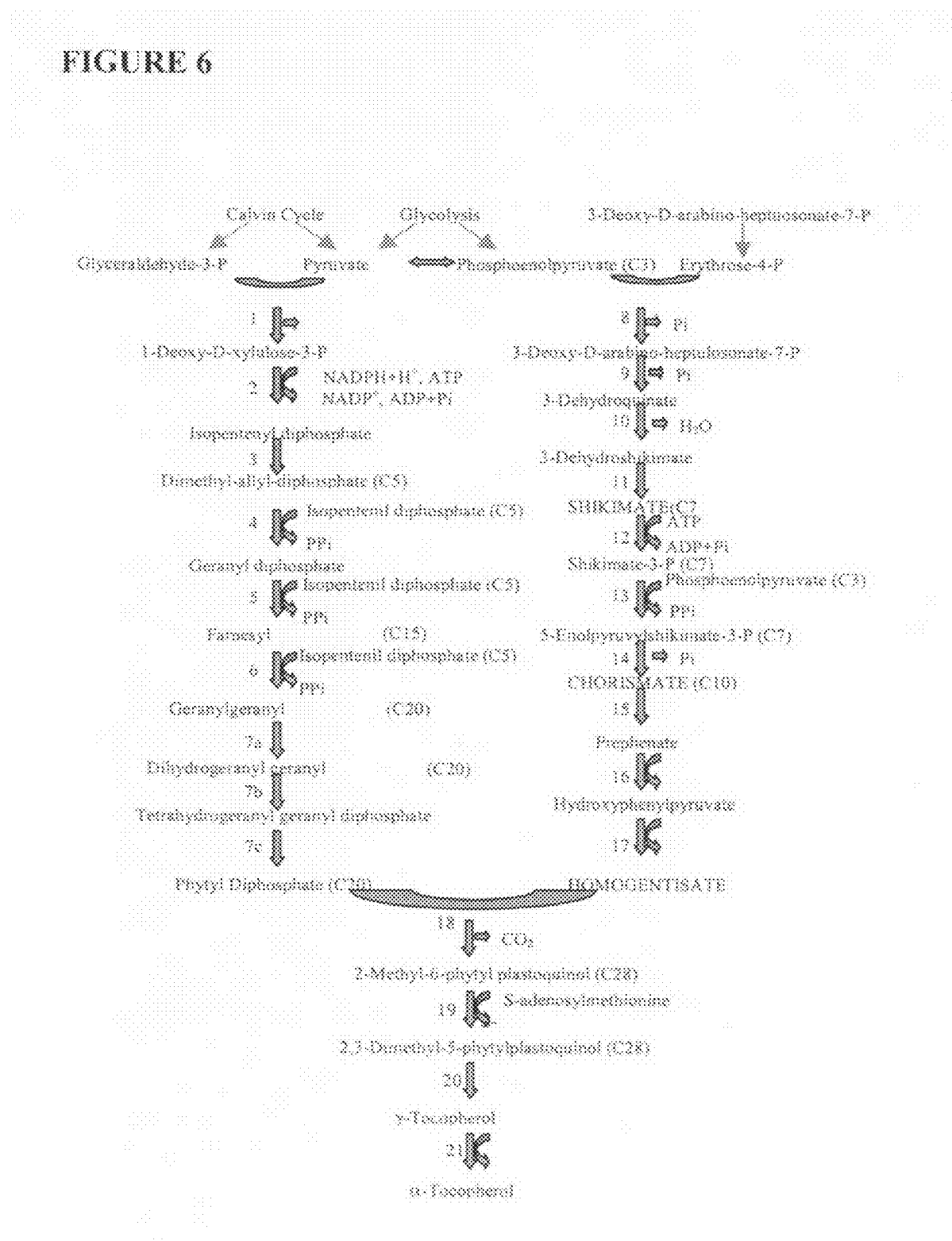
FIG. 6 depicts the tocopherol biosynthetic pathway. The steps include 1: 1-Deoxy-D-xylulose-5-P-synthase; 2: multi-step reaction catalyzed by reductase, dehydratases and a kinase; 3: isomerase; 4-6: consecutive additions of the C5-unit isopentenyl diphosphate to form geranylgeranyl diphosphate; 7a-c: geranylgeranyl reductase; 8: 3-Deoxy-D-arabino-heptulosonate-7-p synthase; 9: 3-Dehydroquinate synthase; 10: 3-Dehydroquinate dehydratase-shikimate dehydrogenase; 11: 3-Dehydroquinate dehyratase-shikimate dehydrogenase; 12: Shikimate kinase; 13: 5-Enolpyruvylshikimate-3-P synthase; 14: chorismate synthasee; 15: chorismate mutase; 16: prephenate dehydrogenase; 17: 4-hydroxyphenylpyruvate dioxygenase; 18: tocopherol prenyl transferase; 19: methyl transferase 1; 20: tocopherol cyclase; and 21: γ-tocopherol methyl transferase. See, also, Munne-Bosch (2002) *Critical Reviews in Plant Sciences* 21:31-57.

There are many potential systematic approaches for refining the selection of genes to be targeted by the final multiZFP-TF. To this end, small arrays containing about five to seven multiZFP-TFs are tested in parallel for their capacity to enhance total tocopherol levels and the level of pathway intermediates. The first multiZFP-TF targets the three genes that control the lefthand side of the synthesis pathway detailed in FIG. 6 (steps 1, 3, and 7a-c); the second targets the three genes at the start of the righthand side of the pathway (FIG. 6; steps 8, 9, and 10/11); the third targets the next three genes in righthand side of the pathway (FIG. 6; steps 12-14); the fourth targets the last three genes on the righthand side of the pathway (FIG. 6; steps 15-17); and a fifth targets the three genes prior to GMT at the end of the pathway (FIG. 6; steps 18-20). In addition, the limits of this approach are tested by building two larger multiZFP-TFs: the first combines ZFPs targeting the first six genes of the righthand side of the pathway, and the second combines all nine genes from the righthand side of the pathway. This provides an invaluable systematic insight into the limits of multigene regulation with respect to the number of genes that can be regulated simultaneously by one multiZFP-TF.

The multiZFP-TFs are transiently transfected into protoplasts to assess their effect on cognate gene expression. MultiZFP-TFs that retain the capacity to activate three target genes >3-fold are retained. For multiZFPs failing to activate >3 fold, optimization studies are conducted, including manipulating the variables (e.g., number and position of activation domains and ZFPs, etc. . . . ), as well as testing activation domains other than C1. We have previously shown in mammalian systems that different activation domains have promoter context-dependent differential efficacy. See, e.g., Liu et al. (2001) *J Biol Chem* 276:11323-34. As a corollary, we have cloned several other plant activation domains that similarly provide us with the potential to optimize the activity of the ZFP-TFs generated in this study. These include the maize-derived activators ZmOp2 (Schmitz et al. (1997) *Nucleic Acids Res* 25:756-63), Vp1 (McCarty et al. (1991) *Cell* 66:895-905), and *Arabidopsis*-derived activators AtERF5 (Fujimoto et al. (2000) *Plant Cell* 12:393-404), and AtOBP2 (Kang et al. (2000) *Plant J* 21:329-39). Assessment of gene expression in protoplasts validates the effectiveness of the multiZFP-TFs as transcriptional activators.

Example 7

Analysis of Tocopherol Levels in MultiZFP-TF Transgenic Plants

To evaluate the extent to which flux through the tocopherol synthesis pathway is upregulated in vivo to increase the level of total tocopherols, transcriptionally validated multiZFP-TFs are stably transfected the into *Arabidopsis* and adult plants generated. The effects of the seven initial multiZFP-TFs on total tocopherol synthesis is analyzed by measuring the levels of select intermediate metabolites throughout the pathway. Seed analysis is conducted approximately 6 months post transfection. Leaf analysis is conducted after approximately 3 months post transfection. Significant (>3-fold) increases in any intermediate product indicate that the multiZFP-TF has overcome a rate-limiting block in the pathway.

Thus, a subset of genes whose activity level is most critical to regulating the throughput of the tocopherol synthesis pathway is identified.

Based on the foregoing results, a single multiZFP-TF that contains the ZFPs that target the most critical (up to 8) rate-limiting genes in tocopherol synthesis is constructed. This multiZFP-TF is stably transfected into plants and the levels of total tocopherol synthesis measured. Multi-ZFPs that achieve a >3-fold increase in the level of total tocopherols in *Arabidopsis* seed oil are used. A >3-fold increase in total tocopherol, combined with a >80-fold increase in the conversion of γ-tocopherol may result in a massive (>200-fold) and economically valuable increase in the final level of α-tocopherol.

Example 8

Selection of DNA Sequence-Specific Zinc Finger Proteins

Multiple (e.g., two) finger modules are selected as parts of 3-finger structures. Residues in two neighboring fingers are varied while the sequence of the remaining finger is kept fixed to limit the combinatorial complexity of the selection process (FIG. 2b). Each of the two libraries thus generated (Lib12, as in the top panel of FIG. 2a; Lib23, as in the lower panel of FIG. 2b) encodes variants of a three-finger DNA-binding domain based on that of the transcription factor Zif268. Lib12 contains randomizations in all the base-contacting positions of Finger 1 and most base-contacting positions of Finger 2 (the only limitation in the current libraries is that these two-finger modules will prefer to have a guanine residue (G) at the 5' end of the six-base pair subsite). Conversely, Lib23 contains randomizations in most of the base-contacting positions of Finger 2 and in all the base-contacting positions of Finger 3 (the only limitation in the current libraries is that these two-finger modules will prefer to have a G at the 3' end of the six-base pair subsite).

Each library contains members that are randomized in the α-helical DNA-contacting residues of two neighboring zinc fingers. We have previously shown that the simultaneous randomization of positions from adjacent fingers is crucial for obtaining optimal contacts at the finger-finger interface (side chains from neighboring fingers can co-operate in base pair recognition at the adjoining edges of the two DNA subsites). See, e.g., Isalan et al. (1998) *Biochemistry* 37:12026-33; Isalan et al. (2001) *Nat Biotechnol* 19:656-60; Isalan et al. (2001) *Methods Enzymol* 340:593-609. Selection in these libraries is facilitated because the randomized sequences do not encode all 20 amino acids, but instead encode only those residues that most frequently function in sequence-specific DNA binding from their respective α-helical positions. See, e.g., Pavelitch & Pabo (1991) *Science* 252:809-17. Excluding the residues that do not frequently function in DNA recognition may reduce the library size and facilitate rapid convergence in the selection process. Phage selections from Lib12 are performed using any DNA sequence of the form 3'-NNN NNG GCG-5' and phage selections from Lib23 can use any sequence of the form 3'-GCG GNN NNN-5'. This procedure gives a master library of fingers that recognize any sequence of the form NNNNNG and of fingers that recognize any sequence of the form GNNNNN. Combining all such fingers in any order gives us immense versatility in recognition. Multiple units of the 2-finger master library will be linked to form 4-finger or 6-finger ZFPs that recognize 12 or 18 base pair sequences with very high specificity (FIG. 2a). Using this approach, ZFPs can be designed to uniquely recognize almost any DNA sequence within a specific target gene promoter.

What is claimed is:

1. A method of modulating the expression of two or more endogenous genes in a cell, the methods comprising introducing into said cell a protein comprising two or more engineered zinc finger domains, wherein each zinc finger domain comprises at least two fingers, and each zinc finger domain binds to a target site in a different endogenous gene, such that the expression levels of the two or more endogenous genes are modulated.

2. The method of claim 1, wherein the protein further comprises at least one functional domain.

3. The method of claim 2, wherein the functional domain comprises an activation domain.

4. The methods of claim 2, wherein the functional domain comprises a repression domain.

5. The method of claim 1, wherein the endogenous genes are involved in a metabolic pathway.

6. The method of claim 1, wherein the endogenous genes are plant genes.

7. The method of claim 6, wherein the endogenous genes are involved in tocopherol synthesis.

8. The method of claim 1 further comprising linker molecules between the zinc finger domains.

9. The method of claim 1, wherein the protein modulates expression of three or more endogenous genes.

10. The method of claim 1, wherein a nucleic acid encoding the protein is introduced into and expressed in the cell.

11. The method of claim 1, wherein the endogenous genes encode one or more enzymes.

12. The method of claim 11, wherein the endogenous genes are involved in tocopherol synthesis.

13. A cell in which two or more endogenous genes are modulated, the cell produced by the method of claim 1, wherein the cell is an isolated cell or a non-human cell.

14. The cell of claim 13, wherein the cell is a eukaryotic cell.

15. The cell of claim 14, wherein the cell is a plant cell.

16. The cell of claim 14, wherein the cell is an animal cell.

17. The cell of claim 16, wherein the cell is an isolated human cell.

* * * * *

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: general
      sequence
<220> FEATURE:
<221> NAME/KEY: SITE
<222> LOCATION: (2)..(5)
<223> OTHER INFORMATION: where Xaa is any amino acid
<220> FEATURE:
<221> NAME/KEY: SITE
<222> LOCATION: (4)..(5)
<223> OTHER INFORMATION: where Xaa may be present or absent and when
      present Xaa is any amino acid
<220> FEATURE:
<221> NAME/KEY: SITE
<222> LOCATION: (7)..(18)
<223> OTHER INFORMATION: where Xaa is any amino acid
<220> FEATURE:
<221> NAME/KEY: SITE
<222> LOCATION: (20)..(24)
<223> OTHER INFORMATION: where Xaa is any amino acid
<220> FEATURE:
<221> NAME/KEY: SITE
<222> LOCATION: (23)..(24)
<223> OTHER INFORMATION: where Xaa may be present or absent and when
      present Xaa is any amino acid

<400> SEQUENCE: 1
```

```
-continued

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa His
        20                  25
```